United States Patent [19]

Speck et al.

[11] Patent Number: 5,232,685
[45] Date of Patent: Aug. 3, 1993

[54] NONIONIC X-RAY CONTRAST MEDIUM WITH HIGH IODINE CONTENT

[75] Inventors: Ulrich Speck; Peter Blaszkiewicz, both of Berlin, Fed. Rep. of Germany

[73] Assignee: Schering Aktiengesellschaft, Berlin and Bergkamen, Fed. Rep. of Germany

[21] Appl. No.: 964,687

[22] Filed: Oct. 22, 1992

Related U.S. Application Data

[62] Division of Ser. No. 607,115, Nov. 2, 1990, Pat. No. 5,183,654.

[30] Foreign Application Priority Data

Nov. 3, 1989 [DE] Fed. Rep. of Germany ....... 3937118

[51] Int. Cl.$^5$ ............................................. A61K 49/04
[52] U.S. Cl. .......................................... 424/5; 424/4; 564/153
[58] Field of Search ................ 564/153, 156; 514/613, 514/617; 424/4, 5

[56] References Cited

U.S. PATENT DOCUMENTS

| | | | |
|---|---|---|---|
| 4,001,323 | 1/1977 | Felder et al. | 424/5 |
| 4,250,113 | 2/1981 | Nordal et al. | 424/5 |
| 4,283,381 | 8/1981 | Speck et al. | 424/5 |
| 4,348,377 | 9/1982 | Felder et al. | 424/5 |
| 4,364,921 | 12/1982 | Speck et al. | 424/5 |

OTHER PUBLICATIONS

USAN and the USP Dictionary of Drug Names, USAN 1992, 1961–1991 cumulative list, p. 324.

Primary Examiner—Richard L. Raymond
Assistant Examiner—Shailendra Kumar
Attorney, Agent, or Firm—Millen, White, Zelano & Branigan

[57] ABSTRACT

5-Hydroxyacetamido-2,4,6-triido-isophthalic acid-(2,3-dihydroxy-N-methyl-propyl)-(2-hydroxy-ethyl)-diamide is outstandingly suitable as x-ray contrast medium.

4 Claims, No Drawings

NONIONIC X-RAY CONTRAST MEDIUM WITH HIGH IODINE CONTENT

This is a division of application Ser. No. 07/607,115 filed Nov. 2, 1990 now U.S. Pat. No. 5,183,654.

This invention relates to a triiodinated isophthalic acid diamide, processes for its production, x-ray contrast media containing it as well as its use for the production of x-ray contrast media.

Prerequisites for a specific and successful therapy are an exact diagnosis. Precisely in the diagnostic field the possibilities in past years have increased very greatly, and x-ray diagnosis is able to represent each anatomical detail selectively and with great accuracy. But in many cases the corresponding structures are visible only by the use of x-ray contrast media. This holds particularly for the blood vessels, and the development of very fine catheters and a further development of x-ray technology also play a greater role. From the more diagnostic representation of the blood vessels by catheters and x-ray contrast media, a great many slightly invasive, inexpensive treatment methods have been developed in the meantime. Thus, for example, it is possible to expand even coronary arteries directly after the representation of a stenosis in the x-ray image with the help of special catheters by "inflation" of a balloon so that an approximately normal blood flow is again produced. By repeated injection of contrast media the exact position of the balloon and the expansion of the artery can be followed step by step. In this way the patient can be spared very expensive and stressful openheart surgery. Another therapeutic use in connection with the vessel representation by catheters and contrast media is the embolizing of vascular malformations or of vessels that supply tumors. Here too the entire process is monitored by the frequently repeated injection of contrast media.

In contrast with the normal x-ray technology, computer-assisted tomography provides sectional pictures through the body, which achieve a very good spatial resolution. Although the density resolution of the computer-assisted tomography is markedly higher than the density resolution of the conventional projection radiography, for surer diagnosis of many pathological changes contrast media are still necessary. It has proved particularly advantageous that newer equipment for an individual shot (layer) needs less than a second. Since then, for characterizing pathological changes not only the contrast media content of a lesion at a given moment is available. After quick intravenous injection, the inflow and outflow of the contrast medium can be measured exactly and essential additional information, for example, on the blood supply and the structure of a tumor, can be obtained from it. Since as a rule only one layer can be observed after each individual contrast medium injection, repeated injections are necessary.

Also in the representation of the urinary tract it has been shown that the quick injection of a high contrast medium dose leads to the best results.

Caused by these developments, the requirements on the quality of the x-ray contrast media has constantly increased.

1) The Concentration

The x-ray density of a contrast medium depends on the iodine concentration in the solution used as the sole parameter, as long as the contrast medium is not diluted. This is especially the case in angiography, if the contrast media are injected with high speed by catheter into the blood vessels: the contrast medium displaces the blood. It is better suited to represent the finest blood vessels, the higher the iodine concentration. Contrast media with extremely high iodine concentration are especially useful if it is a matter of determining whether a blood vessel is completely occluded or a fine channel still exists as a connection to intact peripheral vessels and/or whether peripheral tissues can be supplied with blood by fine bypasses (collaterals). Further, a high iodine concentration is very important if the shooting conditions are otherwise unfavorable, for example since the radiation passage through the body of a heavy patient can be very long.

In a series of other examinations highly concentrated contrast media are also desired, either since the dilution in the body otherwise becomes too great (injection in the heart ventricles, the aorta or intravenous digital subtraction angiography) or since simply for practical reasons the injection volume for achieving a specific dose (g iodine/patient or g iodine/kg of body weight) is to be kept as small as possible.

The x-ray contrast media available so far reach at most a practically usable iodine concentration of 320–370 mg/ml. The reason for this is that at higher concentration they become too viscous and/or too poorly compatible. Compatibility problems arise above all by the high osmolality of the solutions at high iodine concentration.

The Viscosity

X-ray contrast media are generally highly concentrated solutions (50 to greater than 80% by weight). These solutions can become very viscous, partially simply because the water content is clearly below 1 g per ml of solution. On the other hand the use of the contrast media often requires the very quick injection of considerable volumes (30–100 ml) as much as possible by needles that are not too thick or—still more problematical—the injection through catheters up to over a meter long that have to contain in part several very narrow channels to allow, besides the contrast medium application, also filling a balloon or measurement of local blood pressure. Although in some techniques pressure injectors are already used, the viscosity of the contrast medium solutions have to be limited to about 10 cP at 37° C.

Besides poor injectability, more highly viscous contrast media also have the drawback of poor miscibility with blood (schlieren formation instead of homogeneous filling of the heart cavities or blood vessels) and obstruction of the passage through capillaries, for example, of the lung (M. Langer, R. Felix, R. Keysser, U. Speck, D. Banzer: Influencing the imaging quality of i.v. DSA by the iodine concentration of the contrast medium. Digit. Bilddiagn. 5: 154–159 (1985)). For all these reasons, x-ray contrast media should be as thin as possible for vasal use.

3) The Osmolality

Since for most uses x-ray contrast media have to contain iodine in very high concentration, the originally developed preparations were very strongly hypertonic toward blood and tissue. This has caused a number of partially to the blood vessels and cardiovascular disorders. In addition, in some examinations the opacification was also adversely affected by great osmotic dilution (urography) of the contrast media.

In the meantime, improvements have been made by new nonionic contrast media (B. Hagen: Iohexol and iopromide—Two new non-ionic water-soluble radiographic contrast media: Randomized, intraindividual double-blind study versus ioxaglate in peripheral angiography. In Contrast Media, edited by Volker Taenzer and Eberhard Zeitler (1983), Georg Thieme Verlag, pp. 104-114). However, in the painful indications the more contrast-rich, highly concentrated preparations (350-370 mg of iodine/ml) cannot be used, since they with greater than 750 mosm/kg of $H_2O$ still exhibit the 2.5-fold osmolality of the blood and thus are too painful.

4) Solubility

The water-soluble x-ray contrast media without exception are derived from triiodine benzene. This compound itself is practically insoluble and quite toxic. On the molecule there remain 3 positions which can be substituted with side chains for improvement of the solubility and compatibility. Both properties are easier to optimize, the more extensive the side chains become. But great substituents at the same time cause a relative decrease of the iodine content in the molecule (in percent of the molecular weight), an undesirable increase of the viscosity as well as a further decrease of the water content—in any case already little—of the highly concentrated solutions, since at a given iodine concentration each increase of the amount of organic substance in the solution is at the expense of the portion of water.

Therefore a compromise has to be found between as high a water solubility as possible and a good compatibility with as small side chains as possible.

The compounds listed in the following table as 2) to 6) are regarded as the most suitable contrast media at present. It is recognized that molecular weights from 777 to 821 with an iodine content of 46-49%, a viscosity of 8.1 cP (350 mg of I/ml, 37° C.) and an osmolality of 680 mosm/kg of $H_2O$ (370 mg of I/ml) and an $LD_{50}$ value (mouse) of 15 g of iodine/kg can be considered as attainable values in the most favorable case, and it is to be noted that at present no compound exhibits these optimal values at the same time.

TABLE

Properties of contrast media for angiography, urography and computer-assisted tomography

| | Molecular weight | Iodine content | Viscosity cP (37° C., 370 or 350* mg I/ml) | Osmolality mosm/kg $H_2O$ | $LD_{50}$ mouse i.v. g I/kg |
|---|---|---|---|---|---|
| 1) Example 1 of this invention | 747 | 51 | 6.6 | 590 | 18 |
| 2) Iopromide | 791 | 48 | 9.5 | 770 | 15 |
| 3) Iopamidol | 777 | 49 | 9.4 | 830 | 15 |
| 4) Iohexol | 821 | 46 | 10.5* | 820* | 15 |
| 5) Iomeprol | 777 | 49 | 8.6 | 680 | 14 |
| 6) Ioxilan | 791 | 48 | 8.1* | 700* | 15 |

But now in the meantime another increase in requirements can be noted: repeated injections even in previously greatly damaged vessel areas, the elimination of earlier used premedication with analgesics, getting by without using anesthesias or adding of local anesthetics to the contrast medium solution, the higher dosages as a whole and the partially repeated examination and/or treatment of the elderly and very sick patients have intensified the desire for contrast media with still lower osmolality and thus further improved compatibility.

For the often repeated necessary expansion of individual sections of the arteries in one and same patient such improved compatible contrast media are generally a prerequisite to obtaining the consent of the respective patient for this type of therapy. Since moreover (see above) essential practical properties of the finished contrast medium solution such as its injectability through very fine catheters and the flow and contrast properties in the blood vessels depend directly on the viscosity, it is desirable also to have contrast media available whose viscosity data in comparison with previously known media are lowered.

Therefore there is a need for x-ray contrast media, which meet these increased requirements and it is important not to improve an individual property at the expense of other important values but to find substances that meet many requirements as much as possible.

This has been achieved by the present invention.

In European patent application with publication number 0 015 867 (U.S. Pat. No. 4,364,921), compounds are described which come under claimed general formula I

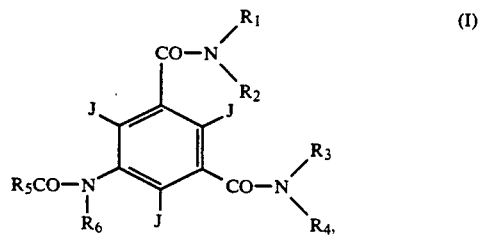

in which the amide radicals —CO—N.$R_1R_2$ and —CO—N.$R_3R_4$ differ from one another and $R_1$ means a hydrogen atom or a lower alkyl radical, $R_2$ means a straight-chain or branched-chain mono- or poly-hydroxy alkyl radical, $R_3$ means a hydrogen atom or a lower alkyl radical, $R_4$ means a straight-chain or branched-chain mono- or poly-hydroxy alkyl radical, $R_5$ means a lower alkyl or a lower hydroxy alkyl or a lower alkoxy lower alkyl group, and $R_6$ means a hydrogen atom or an optionally hydroxylated lower alkyl radical.

In this case, iopromide (examples 6, 7, 8), which is available on the market as Ultravist ®, was recognized as the most suitable compound (see table).

It has now been found that surprisingly 5-hydroxyacetamido-2,4,6-triiodoisophthalic acid-(2,3-dihydroxy-N-methylpropyl)-(2 hydroxy-ethyl)-diamide meets the above-mentioned conditions.

This compound was not emphasized in EP 0 015 867.

It was shown that the new compound, despite a 5-2% increased iodine content, is surprisingly very water-soluble. The distribution according to the invention of the hydrophilic substituents around the triiodinated aromatic substances leads, in contrast with the earlier described compounds, to a compatibility improved in many respects.

As can be seen from the table, compound No. 1 according to the invention combined in itself the most favorable values each of all six contrast media. The viscosity and osmolality values, in comparison with the best compound (iopromide) mentioned in EP 0 015 867, were improved by 30.5% and 23.4%, respectively; on the other hand, the greatest improvements within the previously known five contrast media are only 22.9% (Iohexol/Ioxilan) or 18.1% (Iopamidol/Iomeprol) and are even distributed between two different compounds.

The $LD_{50}$ values (mouse) are the most favorable of the table. Because of the outstanding properties of the compounds according to the invention it is possible, without damaging the blood vessels, even under the most unfavorable conditions to make visible very fine or vessels poorly supplied with blood. A relatively particularly small damage to the blood components and cell membranes occurs. The good compatibility of the new x-ray contrast medium makes possible its use not only in higher concentration than up to now but also in very high dosage, in very sensitive and previously damaged vessel areas or patients with numerous diseases, including those of the cardiovascular system. The new contrast medium, because of the rapid injectability, the smooth passage through the lung and the very quick, selective renal excretion is also especially well suited for computer-assisted tomography, intravenous digital subtraction angiography as well as urography.

Finally it is to be noted that the nonionic x-ray contrast media preferred today are expensive to produce. Because of the very high amounts per patient (up to more than 200 g), the contrast media are an essential cost factor at least of one part of radiological examinations. Therefore it is an advantage of the described contrast medium that the more favorable properties were achieved without the production costs being further increased.

The new contrast medium is marked by good chemical stability. The pharmaceutical preparation can generally be matched to any specific needs of the user. For intravascular injection or infusion, aqueous solutions with a contrast medium content corresponding to 50 mg of iodine/ml to 450 mg of iodine/ml, preferably 100 to 420 mg of iodine/ml, are suitable. These solutions can contain physiologically compatible buffers (bicarbonate, phosphate, citrate, Tris, etc.), stabilizers (EDTA, DTPA, etc.), electrolytes ($Na^+$, $Ca^{2+}$, $K^+$, $Mg^{2+}$, $HCO_3^-$, $Cl^-$, etc.), substances to match the osmolality (mannitol, glucose, etc.) or also pharmacologically effective substances (vasodilators, anticoagulants, etc.). The same solutions can also be used for representing any body cavities, tissues or other structures, by being directly injected or otherwise introduced into the area to be represented.

Another use of the contrast medium in question can be the oral administration for representation of the gastrointestinal tract. For this purpose, the contrast medium can be provided as powder for the production of a solution before use or as concentrate or as prepared solution. In each case, the contrast medium can contain physiologically compatible buffers, stabilizers, substances for matching the osmolality, pharmacologically effective substances, preservaties, flavors and/or swelling substances.

In general, the medium according to the invention is dosed in amounts from 2–500, most often 20–200 ml/examination.

By addition of the contrast medium to various devices, preparations or pharmaceutical agents used in medicine, its stay in the body can be radiologically controlled.

Finally, the new medium because of its high specific weight, its low viscosity and its physiological properties are also suitable as density gradient media in isopycnic centrifuging for fractionating of biological material (Biological Separations in Iodinated Density Gradient Media, Information Retrieval Ltd., London and Washington, D.C., Ed. D. Rickwood).

The invention relates to a process for the production of 5-hydroxyacetamido-2,4,6-triiodo-isophthalic acid-(2,3-dihydroxy-N- methyl-propyl)-(2-hydroxyethyl)-diamide characterized in that in a way known in the art a compound of general formula II

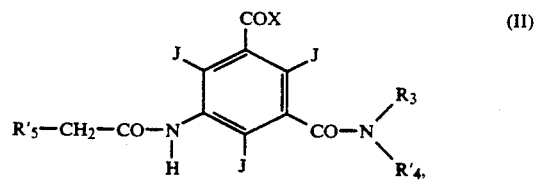

in which
$R_3$ means a hydrogen atom and
$R'_4$ means a 2-hydroxyethyl group or
$R_3$ means a methyl group and $R'_4$ means a 2,3-dihydroxypropyl group, and the hydroxy group(s) optionally is/are protected,
$R'_5$ means a protected hydroxy group,
X means a reactive acid or ester radical,
is reacted with a base of general formula III

in which, if $R_3$ stands for a hydrogen atom and $R'_4$ stands for an optionally protected 2-hydroxyethyl group,
$R_1$ means a methyl group and
$R'_2$ means a 2,3-dihydroxypropyl group, whose hydroxy groups optionally are protected,
or if $R_3$ stands for a methyl group and $R'_4$ stands for an optionally protected 2,3-dihydroxy group,
$R_1$ means a hydrogen atom and
$R_2$ means a 2-hydroxyethyl group, whose hydroxy group optionally is protected,
and then the hydroxy protecting group(s) present is/are cleaved off.

A halogen, such as Cl, Br or I is especially suitable as reactive acid or ester radical X. But basically a conversion can be performed even if X means an acid radical, an alkoxy carbonyl radical or the radical of a reactive ester group, e.g., a usual O alkyl, O aryl or O—$CH_2$—C≡N; preferably a start is made from the starting products with X meaning Cl.

The hydroxyl groups present in starting substances II and III can be present in free or protected form. If these hydroxyl groups are to be present in protected form, all hydroxyl protecting groups are suitable which as is generally known are suitable for intermediate hydroxyl group protection, i.e., which can easily be introduced and can again be easily cleaved by re-formation of the finally desired free hydroxyl group. The protection by esterification, i.e., by introduction of the benzoyl, alkanoyl or acyl radical especially of the acetyl radical, and in case of 1,2-diols also of the cyclic sulfite ester [Topics in Stereochemistry, Vol. 13 (1982), 364]. Suitable protecting groups are also ether groups such as, e.g., benzyl, di- and tri-phenyl methyl ether groups as well as acetal and ketal groups with, e.g., acetaldehyde, acetone and dihydropyran.

The amidation reaction takes place in a suitable solvent at 0°–100° C., preferably at 20°–80° C. Suitable solvents are, i.a., polar solvents. There can be mentioned acetone, water, dioxane, ethylene glycol dimethyl ether, tetrahydrofuran, dimethylformamide, dimethylacetamide, hexametapol, i.a., and their mixtures. Since the amidation reaction proceeds exothermally, it is optionally advisable to cool the reaction mixture slightly to be able to keep the reaction temperature to about 50° C. Since with the amidation reaction, HX is released, for neutralization two equivalent bases, suitably in excess of about 10%, per COX group, are necessary. For the practical execution, dissolved or suspended starting product II is reacted with 2 equivalents of base III or with one equivalent of base III and one equivalent of a base different from III, which then acts as proton acceptor.

Tertiary amines are advantageously used as proton acceptors for the neutralization such as, e.g., triethylamine, tributylamine or pyridine, as well as inorganic bases such as alkali or alkaline-earth hydroxides, carbonates or hydrogen carbonates, e.g., sodium hydroxide, sodium bicarbonate, potassium carbonate, sodium carbonate, calcium hydroxide or magnesium hydroxide.

The inorganic or organic salts precipitating in the course of the reaction are separated in a known way, advantageously with, e.g., the usual ion exchanger columns or by filtration on known adsorbing agents such as, e.g., Diaion or Amberlite XAD–d2 and –4.

The later cleavage of the intermediately introduced protecting groups with release of the finally desired hydroxyl groups also takes place according to methods, which are generally familiar to one skilled in the art. Thus the cleavage of the protecting groups can take place without special reaction step with working up and isolation of the reaction products. But they can also be performed in the usual way in a separate reaction step. Acyl protecting groups can be cleaved for example by alkaline and acetal, ketal or ether protecting groups by acid hydrolysis.

The starting product of formula II is suitably obtained from the easily accessible 5-nitro-isophthalic acid mono ethyl ester. The amide radical $N.R_3R'_4$ is first introduced by aminolysis of the ester group. If the present hydroxyl groups in the amide radical are present in free form, optionally they are protected in the usual way, e.g., as O acetate. The subsequent reduction of the nitro group to the aromatic group also takes place according to the methods known in the art, e.g., with Raney nickel or Pd on $CaCO_3$ in the presence of water or of a lower alcohol such as methanol or ethanol at standard or increased pressure. The 5-aminoisophthalic acid monoamide thus obtained is triiodinated in the usual way and the free carboxyl group is converted into the acid halide group, preferably into the COCl group. If a 2,3-dihydroxypropylamide is introduced into the reaction with thionyl chloride, (as mentioned above) the vicinal diol groups are protected at the same time as sulfite esters. But these hydroxyl groups can also be protected first, e.g., as acetates and then the carboxyl group can be converted to the acid halide. Then the aromatic amino group in the usual way is N-acylated with a reactive $R'_5$-$CH_2$-CO acid derivative to the starting product of general formula II by, e.g., the amine being reacted in an inert solvent such as, e.g., ethyl acetate, ethylene glycol dimethyl ether, dioxane, THF, dichloroethane, pyridine, DMA, DMF, i.a., at temperatures of 0° C. to 100° C. with a reactive $R'_5$-$CH_2$-CO acid derivative, preferably with a corresponding acid halide, especially acid chloride, or but also with a corresponding acid hydride, preferably in the presence of an acid catalyst, such as, e.g., $H_2SO_4$. But the introduction of the $R'_5$-$CH_2$-CO radical can also be performed before the formation of the acid halide.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 37 118.2, filed Nov. 3, 1989, are hereby incorporated by reference.

EXAMPLES

Example 1

5-Hydroxyacetamido-2,4,6-triido-isophthalic acid-(2,3-dihydroxy-N-methyl-propyl)-(2-hydroxy-ethyl)-diamide a)5-amino-2,4,6-triido-isophthalic acid-(2-acetoxy-ethyl)-monoamide 300.96 g (500 mmol) of 5-amino-2,4,6-triido-isophthalic acid-(2-hydroxy-ethyl)-monoamide (GB 1 146 133) is suspended in 300 ml of dioxane. 6.1 g (50 mmol) of 4-dimethylaminopyridine and 56.4 ml (600 mmol) of acetic anhydride is added and the reaction mixture is stirred at an internal temperature of 80° C. After about 1 hour a solution is present, after 2 hours the reaction is quantitative. The reaction solution is cooled to room temperature, diluted with 300 ml of ethyl acetate, inoculated with authentic crystals and the product is crystallized within 5 hours. It is suctioned off, washed with ethyl acetate and dried at 50° C. in a vacuum. 321 g (442.3 mmol)=88.46% of theory is obtained in consideration of a solvate content of 10.2% dioxane.

Analysis in consideration of 10.2% dioxane, 0.25% ethyl acetate and 0.82% water:

| Cld: | C 25.55 | H 2.57 | I 52.45 | N 3.86 | O 15.54% |
|---|---|---|---|---|---|
| Fnd: | 25.83 | 2.68 | 52.21 | 4.05 | % | b) 5-Amino-2,4,6-triido-isophthalic acid (2,3-acetoxyethyl)-monoamide chloride 577 g (800 mmol with consideration of a content of 12% dioxane) of 5-amino-2,4,6-triido-isophthalic acid-(2,3-acetoxy-ethyl)-monoamide is suspended in 2.88 l of dichloroethane, 174.2 ml (2.4 mol) of thionyl chloride is added and the reaction mixture is refluxed at a bath temperature of 120° C. A solution results from the suspension after 1 hour. After 3 hours the reaction is complete. The excess thionyl chloride and the dichloroethane are largely distilled off at reduced pressure. The partially oily, partially solid residue is taken up in 1.3 l of dichloroethane and 228.9 g (800 mmol) of soda decahydrate is added to hydrolyze the sulfinylimide. The color of the suspension changes from orange to bright yellow. It is filtered, the filtration residue is extracted hot with 1.8 l of tetrahydrofuran, filtered, the THF filtrate is concentrated by evaporation and dried in a vacuum at 50° C. 487.1 g (735.4 mmol) of the acid chloride is obtained.

Analysis:

| Cld: | C 21.76 | H 1.52 | Cl 5.35 | I 57.48 | N 4.23 | O 9.66% |
|---|---|---|---|---|---|---|
| Fnd: | 22.15 | 2.03 | 5.67 | 56.98 | 4.03 | % | c) 5-Acetoxyacetamido-2,4,6-triido-isophthalic acid-(2-acetoxy-ethyl)-amide chloride 238.5 g (360 mmol) of 5-amino-2,4,6-triido-isophthalic acid-(2-acetoxy-ethyl)-monoamide chloride is dissolved in 1.19 l of dioxane at room temperature. 146.5 g (1.08 mol) of acetoxyacetyl chloride is added and the reaction solution is stirred at 80° to 90° C. After 12 hours the reaction is practically quantitative. It is cooled to room temperature, inoculated and crystallized for 10 hours. The crystallizate is suctioned off, washed with dioxane and dried in a vacuum at 50° C. 246.5 g (289.67 mmol with consideration of 10.4% dioxane as solvate) = 80.5% of theory of crystalline product.

Analysis with consideration of 10.4% dioxane as solvate.

| Cld: | C 28.23 | H 2.61 | Cl 4.16 | I 44.69 | N 3.28 | O 16.99% |
|---|---|---|---|---|---|---|
| Fnd: | 28.18 | 2.44 | 4.18 | 44.96 | 3.35 | % | d) 5-Hydroxyacetamido-2,4,6-triido-isophthalic acid-(2,3-dihydroxy-N-methyl-propyl)-(2-hydroxy-ethyl)-diamide 533.7 g (0.70 mol) of 5-acetoxyacetamido-2,4,6-triidoisophthalic acid-(2-acetoxy-ethyl)-amide chloride and 300.4 g (1.05 mol) of sodium carbonate decahydrate in 2.67 l of acetone is suspended at room temperature and 95.7 g (0.91 mol) of N-methylamino-propanediol-2,3 is instilled. When the addition of the amine is ended, the suspension is refluxed for 1 hour. It is then cooled to room temperature, the solid is suctioned off and the filtrate is largely concentrated by evaporation. The oily residue is dissolved 1:1 in water, the solution is heated to 50° C. and saponified by continuous addition of 32% NaOH at pH 11-11.5. After the hydrolysis of the acetoxy groups is ended, it is neutralized with HCl and the solution is desalted on 3 liters each of cation and anion exchanger. The aqueous eluate is concentrated by evaporation under reduced pressure to a foam. 450 g of amorphous crude product is obtained. The latter is dissolved in 750 ml of ethanol in boiling heat, inoculated with authentic crystals and crystallized for 12 hours at 60° C. The crystallizate is suctioned off, washed with ethanol and dried for 32 hours at 50° C. in a vacuum. 345.4 g (462.35 mmol) = 66.95% of theory of crystallizate is obtained.

Mp: 258°-260° C.

Analysis with consideration of 0.39% of water and 0.1% of ethanol:

| Cld: | C 25.65 | H 2.74 | I 50.71 | N 5.59 | O 15.29% |
|---|---|---|---|---|---|
| Fnd: | 25.73 | 2.79 | 50.67 | 5.58 | % |

Alternative production of 5-hydroxyacetamido-2,4,6-triidoisophthalic acid-(2,3-dihydroxy-N-methyl-propyl)-(2-hydroxy-ethyl)-diamide 74.85 g (100 mmol) of 5-amino-2,4,6-triido-isophthalic acid-(2,3-diacetoxy-N-methyl-propyl)-amide chloride [(example 8c) in DOS 29 09 439] is dissolved in 225 ml of dry ethyl acetate, 34.13g (250 mmol) of acetoxyacetyl chloride is added and refluxed for 5 hours. The reaction solution is concentrated by evaporation to an oil under reduced pressure, this oil is dissolved in 225 ml of acetone, mixed with 57.23 g (200 mmol) of soda decahydrate and 9.16 g (150 mmol) of ethanolamine and stirred for 5 hours at room temperature. The suspension is then filtered and the filtrate is concentrated by evaporation to an oil. The oil is dissolved in 300 ml of water, the solution is heated to 50° C. and the O acetate groups are saponified by addition by portions of concentrated sodium hydroxide solution at pH 11-11.5. After the hydrolysis is completed, it is neutralized with hydrochloric acid and the solution is desalted with 1 liter each of cation and anion exchanger. The aqueous eluate is concentrated by evaporation to a foam under reduced pressure.

65 g of amorphous product is obtained. The latter is dissolved in 100 ml of boiling ethanol, the solution is inoculated in boiling heat with authentic crystals and crystallized for 12 hours at 60°-70° C. The crystallizate is suctioned off, washed with ethanol and dried for 48 hours at 50° C. in a vacuum. 51.02 g (68.3 mmol) = 68.3% of theory relative to the amine used is obtained.

EXAMPLE 2

1.5 l of an injection solution with 370 mg of I/ml of the compound of example 1d) is produced, by 1089.1 g of the iodine compound being dissolved in 500 ml of bidistilled water, the solution is adjusted with 1.89 g of sodium bicarbonate to pH 7.3, 162.3 mg of CaNa$_2$EDTA is added, it is filled to a volume of 1 liter with bidistilled water, filtered through a filter of pore size of 0.22 microns, poured into Multivials and sterilized for 20 minutes at 120° C.

EXAMPLE 3

1 liter of an injection solution with 370 ml of I/ml of the compound of example 1d) is produced by 726.06 g of the iodine compound being dissolved in 330 ml of bidistilled water, 1211 g of alpha,alpha,alpha-tris-(hydroxymethyl)-methylamine and 108.2 mg of CaNa$_2$EDTA are added, it is adjusted with 5.6 ml of 1N hydrochloric acid to pH 7.3, filtered through a filter with a pore size of 0.22 microns, poured into Multivials and sterilized for 20 minutes at 120° C.

EXAMPLE 4

For oral application, 100 g of the compound of example 1d) is thoroughly mixed with 5 g of saccharose, 0.5 g of flavoring material and 100 mg of polyoxyethylenepolyoxypropylene polymer and packaged sterile. This powder is administered as suspension in water.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of enhancing contrast in an X-ray image of a patient comprising administering 5-hydroxyacetamido-2,4,6-triido-isophthalic acid-(2,3-dihydroxy-N-methyl-propyl)-(2-hydroxy-ethyl)-diamide to a patient.

2. A method of claim 1 which is angiography.

3. A method of claim 1 which is urography.

4. A method of claim 1 which is computer-assisted tomography.